| United States Patent [19] | [11] Patent Number: 4,537,876 |
| --- | --- |
| Blum et al. | [45] Date of Patent: Aug. 27, 1985 |

[54] ACTIVATION OF CATALYSTS FOR SYNTHESIZING METHANOL FROM SYNTHESIS GAS

[76] Inventors: David B. Blum, 108 Tall Oaks Dr., Wayne, N.J. 07470; Abraham P. Gelbein, 45 Headley Rd., Morristown, N.J. 07960

[21] Appl. No.: 556,032

[22] Filed: Nov. 29, 1983

[51] Int. Cl.³ .................... B01J 21/04; B01J 23/06; B01J 23/72
[52] U.S. Cl. .................................... 502/342; 518/700
[58] Field of Search .................... 502/342; 518/700

[56] References Cited

U.S. PATENT DOCUMENTS 3,790,505  2/1974  Casey et al. .................... 502/342
3,888,896  6/1975  Espino et al. .................... 518/700
4,031,123  6/1977  Espino et al. .................... 518/700

FOREIGN PATENT DOCUMENTS 403427  3/1974  U.S.S.R. .................... 502/342

Primary Examiner—W. J. Shine
Attorney, Agent, or Firm—Bert J. Lewen

[57] ABSTRACT

A method for activating a methanol synthesis catalyst is disclosed. In this method, the catalyst is slurried in an inert liquid and is activated by a reducing gas stream. The activation step occurs in-situ. That is, it is conducted in the same reactor as is the subsequent step of synthesizing methanol from a methanol gas stream catalyzed by the activated catalyst still dispersed in a slurry.

5 Claims, No Drawings

ACTIVATION OF CATALYSTS FOR SYNTHESIZING METHANOL FROM SYNTHESIS GAS

BACKGROUND OF THE INVENTION

1. Field of the Invention

The instant invention is directed to a method for activating a methanol synthesis catalyst while the catalyst is dispersed in an inert liquid. More specifically, the instant invention is directed to a method for activating a methanol synthesis catalyst, the catalyst dispersed as a slurry, in-situ in a liquid phase methanol synthesis reactor.

2. Background of the Prior Art

The synthesis of methanol by the catalytic reaction of synthesis gas is an old and well established chemical process. In this process, carbon monoxide and hydrogen are catalytically reacted to form methanol. The catalyst employed usually comprises a mixture of metal oxides. As those skilled in the art are aware, metal oxides are metals having a high oxidation valence state, in which state the metals are stable. However, the metals are effective as methanol synthesis catalysts at lower oxidation states.

To convert the metal oxides to a catalytically active state, effective for use in a methanol synthesis process, requires reduction of the metal oxides to these more active lower oxidation valence states. This, in the prior art, relating to methanol synthesis in a liquid fluidized or slurry reactor system was usually accomplished by contacting the metal oxide catalyst particles with hydrogen gas, in a controlled manner, in a fixed bed reactor whereby the metal oxides were reduced by removal of oxygen as water. This reaction is highly exothermic, requiring that it be carried out very slowly to avoid the development of excess temperature which could result in sintering of the metals and the concomitant reduction in catalyst activity.

Not only are the methods in the prior art for activating methanol synthesis catalysts for use in liquid fluidized or slurry reactor difficult, but, in addition, they do not provide for the possibility of continuous methanol synthesis processing. That is, in the prior art the activation step is conducted in a reactor separate and distinct from the methanol synthesis gas reactor.

A corollary disadvantage in the distinct and separate steps of activating the catalyst and synthesizing methanol lie in the requirement for at least separate gas streams for activation and methanol synthesis. The use of separate gas streams adds difficulty and expense to the overall methanol synthesis reaction.

U.S. Pat. Nos. 3,888,896 and 4,031,123, each assigned to the assignee of the instant application, disclose the use of methanol synthesis catalyst dispersed in an inert liquid as a slurry employed in the catalytic synthesis reaction to form methanol. The disclosure in these patents is limited to providing an active catalyst, in slurry, in the methanol synthesis reaction. No disclosure is made of activating the catalyst in this state.

SUMMARY OF THE INVENTION

It has now been found that the activation of methanol synthesis catalysts can be simplified and improved by activating the catalyst, a group of metals in a high oxidation valence state, while the metals are dispersed in an inert liquid medium. The liquid medium functions as a heat sink for the heat of reaction generated in the reduction of the oxides. This heat sink provides excellent temperature control and permits more rapid activation since the heat sink allows for more rapid rate of reaction because of efficient heat removal. In addition, the improved process of this invention permits activation in the same reactor as is employed in the methanol synthesis itself.

The use of a single reactor for activation and synthesis also permits, in a preferred embodiment, the utilization of the methanol synthesis feed gas as the reducing gas. Not only does this provide a simplification of the overall process, but furthermore allows for continuous addition of fresh catalyst and removal of the spent catalyst from the reactor system in a continuous manner without shutdown of the synthesis reaction.

In accordance with the instant invention a method for activating a catalyst for synthesizing methanol from synthesis gas is provided. In this method, a methanol synthesis catalyst is dispersed in an inert liquid and disposed in a methanol synthesis reactor. The thus formed slurry is then contacted with a reducing gas stream whereby the catalyst in the slurry is activated.

DETAILED DESCRIPTION

The present invention is directed to a method for activating a methanol synthesis catalyst which incorporates the features of slurrying the catalyst with an inert liquid and activating the slurry catalyst in-situ in the reactor employed in the methanol synthesis.

Catalysts employed in the catalytic formation of methanol from synthesis gas are well known to those skilled in the art. These catalysts are metal, supplied at stable higher oxidation states, usually as oxides. The metal are reduced to a lower valence state whereby they are active as catalysts in the catalytic formation of methanol from synthesis gas. Many combinations of metals in higher valence states are known to those skilled in the art as useful as catalysts in the synthesis of methanol. Typically the catalyst used in so called low pressure methanol synthesis is a combination of copper, zinc and aluminum oxides in various concentrations with or without one or more modifiers. In applications where "high pressure" methanol synthesis takes place the usual metal catalyst includes a combination of copper, zinc, chromium and aluminum oxides again with or without one or more modifiers.

The gas stream employed to activate the methanol synthesis catalysts are reducing gases since the activation step comprises a reduction of the valence state of suitable metals. Since a reducing stream is employed, such stream usually includes hydrogen. Several such gas streams are within the contemplation of this invention. In one preferred embodiment, hydrogen is diluted with an inert gas. A preferred inert gas is nitrogen. In this embodiment, the hydrogen comprises 1 to 99% by volume, based on the total volume of the hydrogen-nitrogen mixture. More preferably, the hydrogen concentration varies from 2% to 98% by volume. Still more preferably, the hydrogen concentration is 2 to 25% by volume, based on the total weight of the reducing gas.

In another preferred embodiment of this invention, the actual synthesis gas stream is employed as the activating reducing gas. This embodiment obviously simplifies and reduces the overall methanol synthesis reaction process. In this preferred embodiment the reducing gas stream comprises hydrogen and carbon monoxide, the well known reactants in methanol synthesis gas. In addition, in a preferred embodiment employed in the instant invention, this gas stream includes carbon dioxide. A preferred concentration of this gas mixture is a volume ratio of hydrogen to carbon monoxide in the range of 1:1 to 2:1. The preferred overall concentration of carbon dioxide is 0 to 10% by volume, based on the total volume of the reducing gas mixture. Most preferably, the volume ratio of hydrogen to carbon monoxide is 2:1 in the activating gas with 10% by volume of said gas being carbon dioxide.

In the activation step of the process of this invention the reducing gas stream contacts the methanol synthesis catalyst slurry at a temperature in the range of between 150° and 300° C. More preferably, the temperature range at which the activation step takes place is in the range of between 180° and 280° C. Still more preferably, the temperature of activation is in the range of between 200° and 240° C.

The pressure during activation is in the range of between 200 and 7000 kiloPascals (kPa). More preferably, the pressure range during activation is in the range of 500 and 3500 kPa. Most preferably, the pressure range is between 750 and 1000 kPa.

The activating, reducing gas stream flow rate during activation is between 750 and 3000 liters per hour per kilogram of catalyst (l/hr-kg.). More preferably, the reduction gas stream flows at a rate of 950 to 2500 l/hr-kg. Most preferably, the flow rate is in the range of between 1000 and 1250 l/hr-kg.

In the instant invention the catalyst is activated in a slurry, that is, the catalyst is dispersed in an inert liquid. The inert liquid with which the methanol synthesis catalyst is slurried is preferably selected from the group consisting of a hydrocarbon oil, a fuel oil fraction, a molten paraffin wax, an aromatic oil, a silicone oil, a liquid tetrafluoroethylene polymer and a $C_{10}$-$C_{20}$ aliphatic alcohol mixture. It is emphasized that other inert liquids may also be employed but the above-mentioned list is preferred for use in this application. Of the recited group of inert liquids, within the contemplation of this invention, hydrocarbon oils are more preferred. Most preferably, the hydrocarbon oil employed in the process of the instant invention is a mixture of hydrocarbons having 18 to 30 carbon atoms characterized by a boiling temperature, at atmospheric pressure, of from 200° to 425° C.

During the activation of the catalyst, the catalyst particles remain dispersed in the inert liquid. In one preferred embodiment the catalyst is so maintained by means of mechanical stirring. In another preferred embodiment of this invention the particles remain dispersed in the inert liquid by sparging with the reducing gas stream. In yet another preferred embodiment of this invention a combination of mechanical stirring and sparging is employed to maintain the catalyst as a slurry.

In still another preferred embodiment of this invention the catalyst is maintained in the slurry by continuous circulation of the slurry in a closed path. This latter method permits yet another advantage of the process of the instant invention over those of the prior art. That is, in this embodiment continuous methanol synthesis can be practiced. As those skilled in the art are aware, catalysts lose their effectiveness over time. By the in-situ process of the instant invention the spent catalyst can be removed from the closed path with simultaneous introduction of new catalyst. The new catalyst is immediately activated and thereafter is effective in the catalytic synthesis of methanol.

In a preferred embodiment the methanol synthesis step of the instant invention comprises catalytically reacting a gas stream, comprising hydrogen and carbon monoxide, in the presence of the activated catalyst of the process of the instant invention, dispersed in the inert liquid in which it was activated. The reaction occurs at a pressure in the range of between 3,500 and 7,000 kPa and a temperature in the range of 225° and 275° C. The synthesis gas is passed throught the reactor at a space velocity in the range of between 1,750 and 9,000 liters per hour per kilogram of catalyst. In a preferred embodiment the synthesis gas stream comprises hydrogen and carbon monoxide in volumetric ratio of 2:1 and carbon dioxide present in a total concentration of 10% by volume, based on the total volume of the gas.

The following example is given to illustrate the scope of the instant invention. Thus, this example should not be construed as limiting the invention thereto.

EXAMPLE

A weighted amount (300 grams) of catalyst, a combination of copper, zinc and aluminum oxides was added to 500 cc of a hydrocarbon oil, Witco (trademark) 40, having a boiling temperature between 200° and 425° C., to form a slurry. The resultant slurry was loaded into a 2-liter autoclave equipped with a magnedrive agitator assembly and an automatic temperature controller. The agitator comprised a motor-driven hollow shaft to which an impeller was attached. The slurry was loaded into the autoclave through a loading disposed at the top of the autoclave. Residual wetted catalyst was washed into the autoclave with an additional 500 cc of the oil. This loading procedure was accompanied by operation of the agitator at 900 rpm during which time the autoclave was continuously purged with nitrogen.

After loading of the catalyst slurry the reactor was pressurized with a reduction gas. Upon reaching the desired pressure, the gas was maintained at a constant volumetric flow rate while the reactor was heated slowly to an initial temperature. After reaching the desired initial temperature, the temperature was maintained for 16 hours. After this 16-hour period was reached the temperature was slowly increased to the final maximum temperature of the activation step. The temperature increase was slow and occurred over a 7-hour period. Upon reaching this maximum temperature, it was held for 1 hour. At this point, the in-situ activation step was completed.

The autoclave was then depressurized and repressurized with synthesis gas. Upon repressurization the autoclave was heated to the selected operating temperature and pressure suitable for the catalytic synthesis of methanol.

The methanol synthesis reaction employed the activated catalyst still dispersed in an inert liquid as a slurry. The synthesis gas stream comprised hydrogen and carbon monoxide present in a volume ration of 2:1, respectively. Additionally the synthesis gas stream included 10% by volume carbon dioxide and 15% by volume of inert gases, based on the total volume of synthesis gas stream. The synthesis reaction took place at a pressure of 3500 or 7000 kPa. The temperature of synthesis gas formation ranged from 225° to 275° C. The space velocity of the synthesis gas varied between 1750 to 9000 l/hr-kg of catalyst.

A summary of the activating conditions including activating gas stream constitution, employed in the 16 runs of this example are summarized in Table I.

TABLE I
CATALYST ACTIVATION RUNS

| Technique | Press., kPa | Temp., °C | Composition | Flow Rate, l/hr-kg Catalyst |
|---|---|---|---|---|
| 1 | 875 | 180/240 | 2% $H_2/N_2$* | 1000 |
| 2 | 875 | 200/240 | 2% $H_2/N_2$ | 1000 |
| 3 | 875 | 200/240 | 25% $H_2/N_2$** | 1000 |
| 4 | 875 | 200/240 | 98% $H_2/N_2$*** | 1000 |
| 5 | 875 | 200/240 | 2% $H_2/N_2$ | 1000 |
| 6 | 875 | 200/240 | 2/1 $H_2/CO$ & 10% $CO_2$**** | 1000 |
| 7 | 875 | 200/200 | 2% $H_2/N_2$ | 100 |
| 8 | 875 | 200/260 | 2% $H_2/N_2$ | 100 |
| 9 | 875 | 200/275 | 2% $H_2/N_2$ | 100 |
| 10 | 210 | 200/240 | 2% $H_2/N_2$ | 100 |
| 11 | 2,200 | 180/200 | 98% $H_2/N_2$ | 100 |
| 12 | 2,200 | 180/250 | 98% $H_2/N_2$ | 100 |
| 13 | 1,800 | 200/240 | 2/1 $H_2/CO$ & 10% $CO_2$ | 100 |
| 14 | 3,500 | 200/240 | 2/1 $H_2/CO$ & 10% $CO_2$ | 100 |
| 15 | 7,000 | 200/240 | 2% $H_2/N_2$ | 100 |
| 16 | 7,000 | 180/250 | 98% $H_2/N_2$ | 100 |
| 17 | 7,000 | 200/240 | 2/1 $H_2/CO$ & 10% $CO_2$ | 100 |

*2% by volume $H_2$ in a $H_2$—$N_2$ gas mixture.
**25% by volume $H_2$ in a $H_2$—$N_2$ gas mixture.
***98% by volume $H_2$ in a $H_2$—$N_2$ mixture.
****2:1 by volume $H_2$—$CO_2$ with 10% by volume $CO_2$ and 15% by volume of inert gases.

As Table I indicates, the runs differed from each other in activation pressure, activation temperature, reduction gas composition and/or volumetric flow rate of the reduction gas stream. It is noted that where two temperatures are recited these represent the minimum and maximum temperatures during activation. All the runs employed the same catalyst, the copper, zinc and aluminum oxide mixture, slurried in the same inert liquid, Witco (trademark) 40 hydrocarbon oil.

The thus activated catalyst slurry was then exposed to a synthesis gas stream maintained at various temperature pressures and space velocities to produce methanol. A summary of the reaction conditions employed in the methanol synthesis step is tabulated in Table II. It is emphasized that the catalyst used was the activated form of the catalyst, activated in the activation still slurried in the inert liquid.

TABLE II
REACTION CONDITIONS FOR METHANOL SYNTHESIS

| Condition | Gas Type | Press., kpa | Temperature, °C | Space Velocity l/hr-kg catalyst |
|---|---|---|---|---|
| A | 2/1 $H_2/CO$ | 3,500 | 225–230 | 3,600–4,000 |
| B | 2/1 $H_2/CO$ | 3,500 | 250 | 1,750 |
| C | 2/1 $H_2/CO$ | 3,500 | 250 | 3,700–4,000 |
| D | 2/1 $H_2/CO$ | 3,500 | 250 | 7,000 |
| E | 2/1 $H_2/CO$ | 7,000 | 225 | 4,000 |
| F | 2/1 $H_2/CO$ | 7,000 | 250 | 5,000 |
| G | 2/1 $H_2/CO$ | 7,000 | 250 | 5,500–6,300 |
| H | 2/1 $H_2/CO$ | 7,000 | 275 | 2,300 |
| I | 2/1 $H_2/CO$ | 7,000 | 275 | 4,000 |
| J | 2/1 $H_2/CO$ | 7,000 | 275 | 6,000 |
| K | 2/1 $H_2/CO$ | 7,000 | 275 | 9,000 |

Table III summarizes the methanol synthesis product of the combined activation and synthesis steps. In Table III, the overall combinations of catalyst activation and methanol reaction conditions employed are tabulated with the resultant conversion to methanol in gram moles of methanol per hour per kilogram of catalyst. In addition, Table II provides the conversion, in percent, of hydrogen, carbon monoxide and carbon dioxide.

TABLE III
METHANOL SYNTHESIS RESULTS USING ACTIVATED CATALYST

| Reaction condition | C | | | | | | | | | | | | | | | | |
|---|---|---|---|---|---|---|---|---|---|---|---|---|---|---|---|---|---|
| Activation technique | 1 | 2 | 3 | 4 | 5 | 6 | 7 | 8 | 8 | 9 | 9 | 10 | 11 | 12 | 13 | 14 | 15 16 |
| $H_2$ conv., % | 22.3 | 24.4 | 25.1 | 20.3 | 24.0 | 21.8 | 17.2 | 18.4 | 19.5 | 18.5 | 20.2 | 19.2 | 14.0 | 6.1 | 19.8 | 20.1 | 19.6 6.6 |
| CO conv., % | 18.0 | 24.2 | 26.3 | 20.7 | 22.6 | 22.5 | 17.0 | 17.4 | 18.4 | 16.6 | 20.2 | 19.2 | 13.3 | 5.5 | 22.7 | 21.9 | 19.7 6.2 |
| $CO_2$ conv., % | 2.3 | 1.7 | 1.6 | 0.2 | 0.2 | (0.5) | 2.0 | 2.2 | 0.2 | 3.1 | 2.6 | 3.7 | 3.4 | 3.5 | 1.1 | 1.5 | 2.2 3.7 |
| Methanol productivity, g mol/kg-hr | 8.5 | 12.0 | 12.0 | 9.9 | 10.8 | 10.2 | 8.1 | 8.6 | 8.1 | 8.8 | 10.0 | 9.7 | 6.0 | 3.0 | 10.7 | 10.1 | 9.5 4.0 |

| Reaction condition | G | | | | | | | | | | | | | | | | |
|---|---|---|---|---|---|---|---|---|---|---|---|---|---|---|---|---|---|
| Activation technique | 1 | 2 | 3 | 4 | 5 | 6 | 7 | 8 | 8 | 9 | 9 | 10 | 11 | 12 | 13 | 14 | 15 16 |
| $H_2$ conv., % | — | 42.1 | 44.6 | 40.9 | 39.2 | 43.0 | 35.4 | 36.7 | 37.6 | 36.6 | 37.9 | 34.4 | — | — | 39.9 | 39.5 | 41.1 — |
| CO conv., % | — | 42.1 | 46.0 | 41.0 | 38.4 | 41.7 | 34.8 | 35.4 | 36.3 | 34.6 | 36.8 | 32.7 | — | — | 40.0 | 39.0 | 40.9 — |
| $CO_2$ conv., % | — | 8.3 | 7.3 | 8.9 | 5.2 | 7.2 | 6.0 | 5.6 | 4.8 | 6.3 | 6.2 | 3.5 | — | — | 5.9 | 5.6 | 9.1 — |
| Methanol productivity, g mol/kg-hr | — | 31.0 | 30.0 | 28.3 | 26.4 | 30.9 | 23.3 | 24.8 | 23.7 | 24.3 | 26.0 | 22.7 | — | — | 28.0 | 27.5 | 31.6 — |

| Reaction condition | A | B | D | D | F | H | I | I | I | J | K |
|---|---|---|---|---|---|---|---|---|---|---|---|
| Activation technique | 5 | 1 | 12 | 12 | 17 | 1 | 1 | 11 | 12 | 11 | 12 |
| $H_2$ conv., % | 21.2 | 27.1 | 3.7 | 3.9 | 25.4 | 40.2 | 37.6 | 32.1 | 27.5 | 28.1 | 15.2 |
| CO conv., % | 23.3 | 20.5 | 1.4 | 3.1 | 26.4 | 34.9 | 34.2 | 27.2 | 25.6 | 29.4 | 15.3 |
| $CO_2$ conv., % | 1.0 | 1.0 | 3.3 | 2.7 | 4.4 | (1.5) | (0.6) | 4.3 | 4.4 | 6.5 | 5.0 |
| Methanol productivity, g mol kg-hr | 9.7 | 4.5 | 2.0 | 3.0 | 15.8 | 9.5 | 16.5 | 13.5 | 13.0 | 23.0 | 17.0 |

RESULTS

The above example establishes the adequacy of methanol synthesis produced by the catalytic methanol gas synthesis reaction employing the activation step of this invention over a whole series of conditions. The in-situ reduction of the catalyst is thus seen to be successful.

To illustrate this, reaction conditions C and G are set forth in detail. These represent low severity and high severity reaction conditions, respectively. The resultant methanol productivity was within the range obtained by the catalyst activation methods employed in the prior art. A review of the generated data indicates that the best results were obtained when activation runs 2 and 3 were employed. In these runs a pressure of 875 kPa, a temperature of from 200° to 240° C. and a hydrogen/nitrogen mixture which comprised from 2 to 25% by volume hydrogen and a volumetric flow rate of 100 liters per hour per kilogram of catalyst of reduction gas was employed.

The above embodiments and examples are provided to illustrate the scope and spirit of the instant invention. These embodiments and examples will make apparent, to those skilled in the art, other embodiments and examples. These other embodiments and examples are within the contemplation of this invention. Therefore, the instant invention should be limited only by the appended claims.

What is claimed is:

1. A method for activating a methanol synthesis catalyst for use in a liquid phase methanol process comprising:

forming a slurry of solid metal oxide catalyst particles in an inert liquid, in a methanol synthesis reactor; and activating said catalyst by reducing said catalyst particles with a reducing gas stream containing at least 25% hydrogen at a temperature in the range of between 150°–300° C. and a pressure in the range of between 200 and 7,000 kPa at a reducing gas stream volumetric flow rate in the range of between 750 and 3000 liters per hour per kilogram of catalyst.

2. A method in accordance with claim 1 wherein said reducing gas is synthesis gas.

3. A method in accordance with claim 1 wherein said reducing gas is a mixture of hydrogen, carbon monoxide and carbon dioxide wherein the volumetric ratio of hydrogen to carbon monoxide is between 1:1 and 2:1 and said carbon dioxide comprises 0 to 10% by volume of the total volume of said reducing gas.

4. A method in accordance with claim 1 wherein said catalyst comprises a mixture of copper, zinc and aluminum oxides.

5. A method in accordance with claim 1 wherein said inert liquid is selected from the group consisting of a hydrocarbon oil, a fuel oil fraction, a molten paraffin wax, an aromatic oil, a silicone oil, a liquid tetrafluoroethylene polymer and a $C_{10}$–$C_{20}$ aliphatic alcohol mixture.

* * * * *